(12) United States Patent
Kuri et al.

(10) Patent No.: US 9,675,816 B2
(45) Date of Patent: Jun. 13, 2017

(54) NEUTRON CONTROL DEVICE AND NEUTRON IRRADIATION APPARATUS

(71) Applicants: MITSUBISHI HEAVY INDUSTRIES MECHATRONICS SYSTEMS, LTD., Kobe-shi, Hyogo (JP); OSAKA UNIVERSITY, Suita-shi, Osaka (JP)

(72) Inventors: Shuhei Kuri, Kobe (JP); Toshiharu Takahashi, Kobe (JP); Hiroshi Horiike, Suita (JP); Eiji Hoashi, Suita (JP); Isao Murata, Suita (JP); Sachiko Doi, Suita (JP); Itsuro Kato, Suita (JP)

(73) Assignees: MITSUBISHI HEAVY INDUSTRIES MECHATRONICS SYSTEMS, LTD., Hyogo (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/914,256

(22) PCT Filed: Sep. 5, 2014

(86) PCT No.: PCT/JP2014/073522
§ 371 (c)(1),
(2) Date: Feb. 25, 2016

(87) PCT Pub. No.: WO2015/034058
PCT Pub. Date: Mar. 12, 2015

(65) Prior Publication Data
US 2016/0220839 A1 Aug. 4, 2016

(30) Foreign Application Priority Data

Sep. 6, 2013 (JP) .................................. 2013-185742

(51) Int. Cl.
*A61N 5/00* (2006.01)
*H05H 3/06* (2006.01)
(Continued)

(52) U.S. Cl.
CPC ............. *A61N 5/00* (2013.01); *A61N 5/1077* (2013.01); *G21K 1/10* (2013.01); *G21K 5/02* (2013.01);
(Continued)

(58) Field of Classification Search
CPC .. A61N 5/00; A61N 5/1077; A61N 2005/109; G21K 5/08; G21K 5/02; G21K 5/04; G21K 1/10; H05H 3/06; H05H 6/00
(Continued)

(56) References Cited

U.S. PATENT DOCUMENTS 5,703,918 A * 12/1997 Hiismaki ................. A61N 5/10
376/458
5,903,622 A * 5/1999 Yoon ........................ H05H 3/06
376/110
(Continued)

FOREIGN PATENT DOCUMENTS

JP  2007-95553 A   4/2007
JP  2007-242422 A  9/2007
(Continued)

OTHER PUBLICATIONS

International Search Report and Written Opinion in International Patent Application No. PCT/JP2014/073522, mailed Nov. 11, 2014.
(Continued)

*Primary Examiner* — Michael Maskell
(74) *Attorney, Agent, or Firm* — Kanesaka Berner and Partners LLP

(57) ABSTRACT

The neutron irradiation apparatus includes an introduction tube for introducing a proton beam, a target structure provided in a lower end of the introduction tube, an aluminum fluoride layer disposed below the target structure in an irradiation path of neutrons generated in the target structure, and a heavy water layer placed under the aluminum fluoride
(Continued)

layer in layers. The aluminum fluoride layer is set at a thickness that increases epithermal neutrons. Since use of only the aluminum fluoride layer increases its thickness too much, heavy water is placed. Heavy water moderates neutrons quickly, and allows increasing epithermal neutrons without increasing the thickness. The combination of the aluminum fluoride layer and the heavy water layer allows increasing epithermal neutrons by attenuating only fast neutrons without increasing thermal neutrons. Accordingly, neutron flux with many epithermal neutrons is obtained.

5 Claims, 2 Drawing Sheets

(51) Int. Cl.
*H05H 6/00* (2006.01)
*A61N 5/10* (2006.01)
*G21K 1/10* (2006.01)
*G21K 5/04* (2006.01)
*G21K 5/02* (2006.01)
*G21K 5/08* (2006.01)

(52) U.S. Cl.
CPC ............... *G21K 5/04* (2013.01); *G21K 5/08* (2013.01); *H05H 3/06* (2013.01); *H05H 6/00* (2013.01); *A61N 2005/109* (2013.01)

(58) Field of Classification Search
USPC .............. 250/492.1, 505.1, 515.1, 518.1
See application file for complete search history.

(56) References Cited

U.S. PATENT DOCUMENTS

2012/0330084 A1* 12/2012 Pantell ............... A61N 5/10
600/1
2013/0064338 A1   3/2013 Matsumoto et al.

FOREIGN PATENT DOCUMENTS

| JP | 2009-192488 A | 8/2009 |
| JP | 2013-61295 A | 4/2013 |
| WO | 94/29881 A1 | 12/1994 |

OTHER PUBLICATIONS

Hideki Matsui, Outline of International Fusion Materials Irradiation Facility (IFMIF) Project, Institute for Materials Research, Tohoku University, Japan Atomic Energy Research Institute, The Eleventh Fusion Research Development Problem Study Meeting, Sep. 29, 2003, p. 14, for which an Explanation of Relevancy is attached.
Extended European Search Report in EP Application No. 14842175.3, dated Jul. 18, 2016.
Intention to Grant a Patent in EP Application No. 14842175.3, dated Jan. 27, 2017.

* cited by examiner

NEUTRON CONTROL DEVICE AND NEUTRON IRRADIATION APPARATUS

RELATED APPLICATIONS

The present application is a National Stage of PCT International Application No. PCT/JP2014/073522, filed Sep. 5, 2014, which claims the benefit of priority from Japanese Patent Application No. 2013-185742, filed Sep. 6, 2013.

FIELD

The present invention relates to neutron control devices and neutron irradiation apparatuses for obtaining neutron flux that contains many epithermal neutrons.

BACKGROUND

At present, boron neutron capture therapy (BNCT) is receiving attention as a technology that can selectively kill and treat cancer cells. BNCT requires use of thermal neutrons or epithermal neutrons, thus imposing many constraints such as the necessity for patients to go to a nuclear reactor by which neutrons can be generated and used. Therefore, a small-sized neutron generator that allows generation of neutrons in a hospital has been desired. In a neutron generator, a beryllium or lithium target is bombarded with protons or deuterons accelerated by an accelerator.

As a conventional accelerator, the one as described in Non Patent Literature 1 is known. This accelerator includes an electron cyclotron resonance (ECR) ion source, a radio-frequency quadrupole (RFQ) linac, and a drift tube linac (DTL), which are installed consecutively. In this accelerator, the RFQ linac accelerates deuterons to 5 MeV, and the DTL accelerates them to 40 MeV. A beam of the accelerated deuterons is emitted to liquid lithium flowing over a curved back wall, generating neutrons behind it.

CITATION LIST

Patent Literature

Non Patent Literature 1: Outline of International Fusion Materials Irradiation Facility (IFMIF) Project, Institute for Materials Research, Tohoku University, Japan Atomic Energy Research Institute, Hideki Matsui, The Eleventh Fusion Research Development Problem Study Meeting, Sep. 29, 2003, Page 14

SUMMARY

Technical Problem

Thermal neutrons, which show its intensity peak in the vicinity of a surface layer of a human body, are suitable for treatment against a lesion in the vicinity of a surface layer. However, since thermal neutrons decay in dose as they travel from a surface layer into a deep part, irradiation from outside a human body cannot irradiate a lesion in a deep part with a required amount of neutrons. Thus it is required to open an affected part by an operation to irradiate it with neutrons, for example. On the other hand, epithermal neutrons lose energy in the course of reaching from a surface layer to a deep part, turning into thermal neutrons. Therefore, by irradiating a lesion at a depth up to about 70 mm from a surface layer with epithermal neutrons from outside a human body, the lesion can be treated.

Thus, the present invention has an object of performing control so that epithermal neutrons can be increased for irradiation to treat a deep lesion.

Solution to Problem

According to an aspect of the present invention, a neutron control device includes a fluoride layer containing aluminum fluoride, magnesium fluoride or Fluental, and a heavy water layer containing deuterium. The fluoride layer and the heavy water layer are stacked each other in an irradiation path of neutrons generated in a target irradiated with a proton beam.

In the present invention, the fluoride layer is used as a first moderation layer to moderate high-energy fast neutrons generated in the target. The fluoride layer reduces the energy of fast neutrons to 10 KeV or less while reducing absorption thereof. Since use of only the fluoride layer increases its required thickness, the deuterium layer having a high moderation capability is used as a second moderation layer. By adjusting their thicknesses, an ideal epithermal neutron field in which fast neutron components are reduced while thermal neutrons are not increased car be created.

Advantageously, a plate-shaped first neutron absorber made of cadmium is provided downstream of the heavy water layer. According to this configuration, thermal neutrons generated in the fluoride layer and the deuterium layer can be reduced by cadmium without reducing the epithermal neutron flux intensity. Thus, the thermal/epithermal neutron ratio can be improved while a high epithermal neutron flux can be obtained. In this case, a lead plate is preferably disposed downstream of the first neutron absorber. With this, gamma rays generated by cadmium can be blocked, so that an epithermal neutron flux with a small dose of gamma rays can be obtained.

Advantageously, a plate-shaped second neutron absorber containing boron or lithium is provided around the first neutron absorber. The combination with the first neutron absorber can effectively block low-energy neutrons to block unnecessary neutrons to go around and reach a patient, so that epithermal neutrons can go forward.

According to another aspect of the present invention, a neutron irradiation apparatus includes: a proton beam introduction tube for introducing a proton beam; a target provided at a distal end of the proton beam introduction tube; a graphite body disposed around the target; the neutron control device according to any one of the above; and a neutron moderation tank disposed to surround the graphite body and the neutron control device, into which tank a boric acid solution or another neutron moderator is introduced. The neutron control device is disposed ahead of the proton beam introduction tube.

DESCRIPTION OF EMBODIMENT

Figure 1:
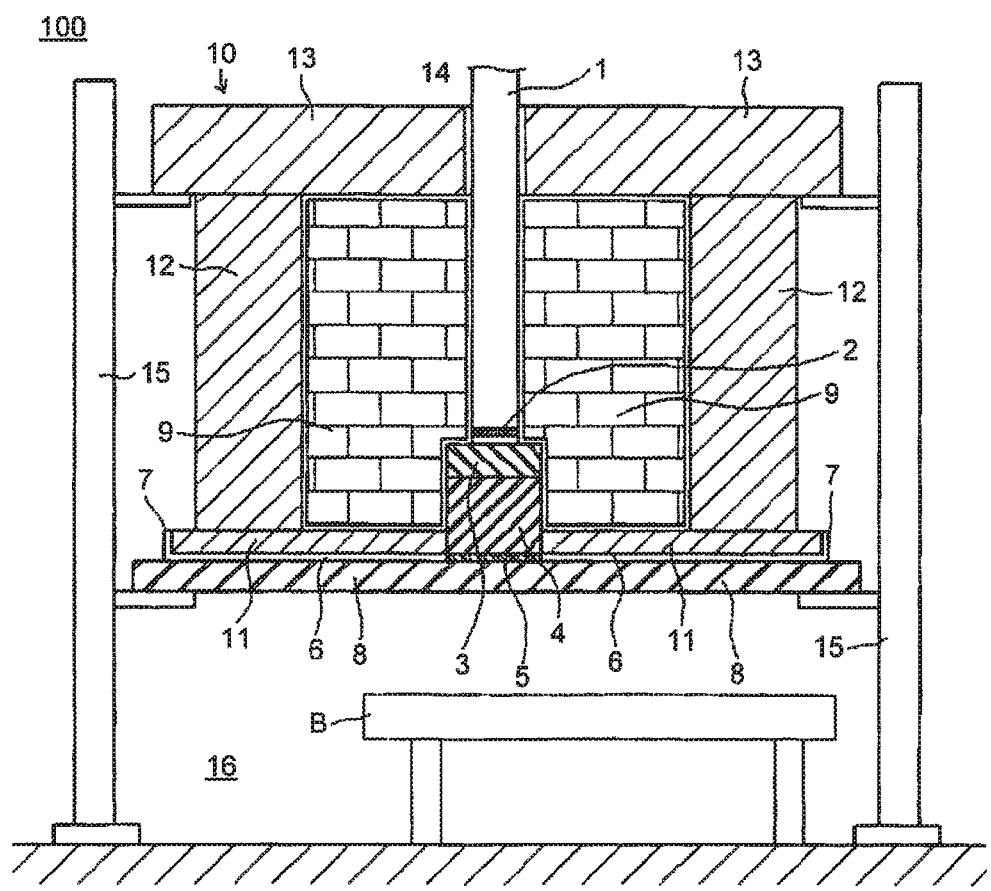
FIG. 1 is a configuration diagram illustrating a neutron irradiation apparatus according to an embodiment of the present invention.

FIG. 1 is a configuration diagram illustrating a neutron irradiation apparatus according to an embodiment of the present invention. A neutron irradiation apparatus 1 includes an introduction tube 1 for introducing a proton beam, a target structure 2 provided in a lower end of the introduction tube 1, an aluminum fluoride layer 3 disposed below the target structure 2 in an irradiation path of neutrons generated in the target structure 2, and a heavy water layer 4 placed under the aluminum fluoride layer 3 in layers. The aluminum fluoride layer 3 and the heavy water layer 4 constitute a moderation layer for controlling the energy of neutrons. The aluminum fluoride layer 3 and the heavy water layer 4 constitute a neutron control device for controlling neutrons generated in the target structure 2.

The introduction tube 1 is connected to an ion source, an accelerator such as an RFQ, and an additional accelerator such as a DTL (not illustrated). The target structure 2 is a structure to circulate liquid lithium as a target in the lower end of the introduction tube 1. The target is not limited to liquid lithium, and may be a solid lithium thin film.

The aluminum fluoride layer 3 constitutes a first moderation layer for neutrons, and is made of a sintered compact of aluminum fluoride powder in a cylindrical pedestal shape. The aluminum fluoride layer 3 may be replaced with a fluoride layer made of magnesium fluoride or Fluental.

The heavy water layer 4 constitutes a second moderation layer for neutrons, and includes a predetermined amount of heavy water and a tank containing the heavy water in a cylindrical pedestal shape with the same diameter as the aluminum fluoride layer 3. The heavy water layer 4 is installed because required moderation only with the aluminum fluoride layer 3 increases its thickness too much. The heavy water layer 4 may be formed with deuterated plastic in a cylindrical pedestal shape with the same diameter as the aluminum fluoride layer 3. The thicknesses of the aluminum fluoride layer 3 and the heavy water layer 4 are determined based on the size, number, and depth of a tumor. A plurality of combinations of the aluminum fluoride layer 3 and the heavy water layer 4 may be placed in layers on the neutron irradiation path.

An inner disk 5, a first neutron absorber, made of a material containing cadmium and having a predetermined diameter is disposed below the heavy water layer 4. The inner disk 5 has a diameter to emit a neutron beam based on the size, number, and depth of a tumor. An outer disk 6, a second neutron absorber, made of a material containing boron and having a toroidal shape is disposed around the inner disk 5. An annular side wall 7 made of a material containing boron is provided around the outer disk 6. As an element contained in the outer disk 6, lithium may be used in place of boron.

A lead layer 8 is provided over the entire lower sides of the inner disk 5 and the outer disk 6. The lead layer 8 has a structure in which a plurality of lead plates formed in a block sheet shape and having a predetermined thickness is arranged circumferentially.

A graphite region 9 for reflecting/moderating neutrons is provided around a distal end and its vicinity of the introduction tube 1, the aluminum fluoride layer 3, and the heavy water layer 4. The graphite region 9 may be made by combining a plurality of blocks of graphite bodies.

The distal end and its vicinity of the introduction tube 1, the aluminum fluoride layer 3, the heavy water layer 4, and the graphite region 9 except the inner disk 5 are enclosed by a tank containing a boric acid solution. A tank 10 includes a lower tank 11 provided horizontally around the heavy water layer 4, a side tank 12 provided around the graphite region 9, and an upper tank 13 provided above the graphite region 9. The upper tank 10 is provided at its center with an opening 14 through which to pass the introduction tube 1.

The above-described structure is supported by a plurality of pillars 15 and an irradiation space 16 is formed lower side thereof. A lesion of a patient placed on a bed B is located directly below the target structure 2 in the irradiation space 16, that is, on the irradiation path of a collimated neutron beam.

In the above configuration, for example, for the accelerator, an electrostatic-type one is used, and its potential is set at Ep=2.4 to 2.8 MeV, IP=15 to 40 mA. For the target, a liquid lithium flow is used.

Using the neutron irradiation apparatus 100, a proton beam is emitted from the accelerator through the introduction tube 1 to the target in the distal end. Neutrons are generated at a rear surface of the target. For neutrons, there are regions of thermal neutrons, epithermal neutrons, and fast neutrons. In the aluminum fluoride layer 3, fast neutrons are moderated to epithermal neutrons of 10 KeV or less mainly by the action of fluorine. The aluminum fluoride layer 3 is set at a thickness that maximizes the number of epithermal neutrons, with which thickness it is too thick to retain its strength. Therefore, by placing heavy water downstream, neutrons are moderated quickly, and epithermal neutrons can be increased without increasing the thickness. The combination of the aluminum fluoride layer 3 and the heavy water layer 4 allows increasing epithermal neutrons by attenuating only fast neutrons without increasing thermal neutrons.

Further, thermal neutron components are removed by the inner disk 5 made of cadmium downstream of the heavy water layer 4 in a neutron irradiation direction. Specifically, thermal neutrons generated in the moderation layer consisting of the aluminum fluoride layer 3 and the heavy water layer 4 are absorbed by the inner disk 5, the neutron absorber. As a result, a neutron flux with a high proportion of epithermal neutrons is obtained.

The outer disk 6 containing boron around the inner disk 5 blocks neutrons deviating from an irradiation area for a patient. The boric acid solution in the tank 10 disposed on a top surface of the outer disk 6 moderates the neutrons, thus facilitating the capture of the neutrons by boron in the outer disk 6. This can block unnecessary neutrons from going around and reaching a patient. Thus epithermal neutrons to be introduced into a patient can reach be irradiated.

Since the graphite region 9 surrounds all of a top surface and a side surface of the aluminum fluoride layer 3, neutrons scatter and reach the heavy water layer 4. Since a side surface of the heavy water layer 4 is surrounded by the graphite region 9 at an upper portion but adjoins the tank 10 of the boric acid solution at a lower portion, thermal/epithermal neutrons going out from here are moderated by the boric acid solution, and are blocked by boron in the outer disk 6.

Further, the lead layer 8 blocks gamma rays caused by moderation and absorption of neutrons. Cadmium in the inner disk 5 produces gamma rays. Therefore, the lead layer 8 is provided downstream of the inner disk 5 to block gamma rays produced in the inner disk 5. Thus, epithermal neutrons can be increased under conditions of a low dose of gamma rays.

A proton beam was emitted by an accelerator of Ep=2.65 MeV, Ip=some 100 μA to the neutron irradiation apparatus 100 above, and the neutron flux intensity and the gamma ray air dose were measured. Since the experimental values below were measured at a current of 236 μA, neutron flux when they are extrapolated to actual equipment of 30 mA is as follows by a proportional calculation.

| Neutron Flux (n/sec/cm$^2$) | | Extrapolation to 30 mA (Actual Equipment) |
|---|---|---|
| | Experimental Value (Iave = 236 μA) | |
| Thermal Neutron: | 4.6 × 10E4 | 5.8 × 10E6 |
| Epithermal Neutron: | 6.4 × 10E6 | 8.1 × 10E8 |
| Fast Neutron: | 9.6 × 10E5 | 1.2 × 10E8 |
| | Experimental Value (Iave = 185 μA) | |
| γ Ray Air Dose (Gy/hr): | 1.5 × 10E−3 | 0.24 |

Figure 2:
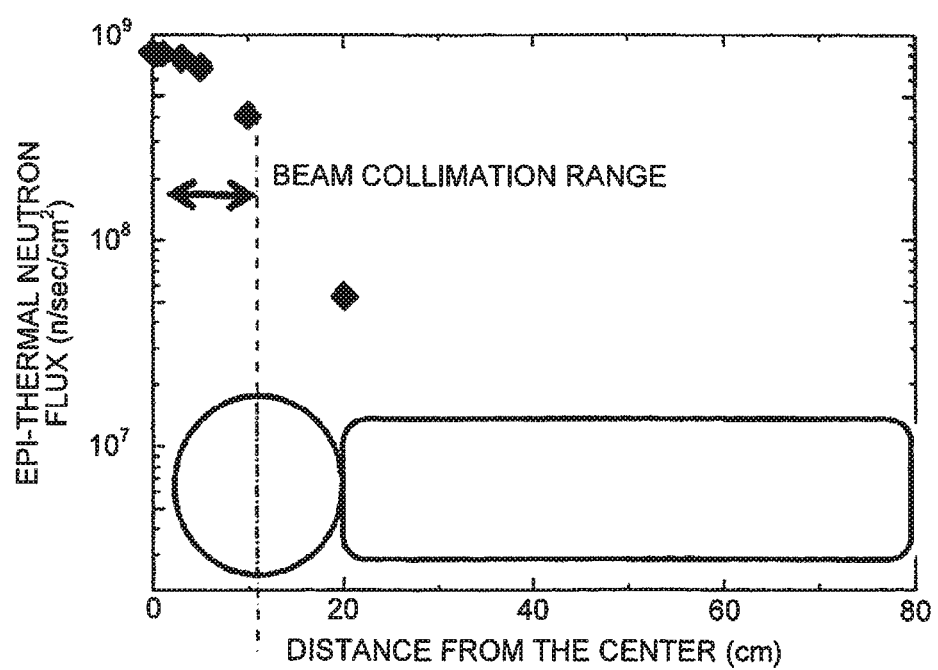
FIG. 2 is a graph illustrating results of collimating neutrons by a neutron control device.

As illustrated in FIG. 2, the radial distribution of the neutron flux intensity was also measured. It has been found that when the radius of the moderation layer is 10 cm, neutron flux of epithermal neutrons is effectively collimated depending on the radius of the moderation layer.

As above, the neutron irradiation apparatus 100 of the present invention can provide neutron flux in which fast neutron components are attenuated, thermal neutrons are reduced, and epithermal neutrons are increased. Thus, it is effective in treating deep lesions. The neutron irradiation apparatus shown in the above embodiment is applicable to something other than BNCT such as a neutron CT device for material inspection and an explosive detector.

REFERENCE SIGNS LIST

100 Neutron Irradiation Apparatus
1 Introduction Tube
2 Target Structure
3 Aluminum Fluoride Layer
4 Heavy Water Layer
5 Inner Disk
6 Outer Disk
10 Tank

The invention claimed is:

1. A neutron control device comprising:
 a fluoride layer containing aluminum fluoride, magnesium fluoride, or Fluental, the fluoride layer being a first moderation layer; and
 a heavy water layer containing deuterium, the heavy water layer being a second moderation layer disposed below the first moderation layer, wherein
 the fluoride layer and the heavy water layer are stacked each other in an irradiation path of neutrons generated in a target irradiated with a proton beam.

2. The neutron control device according to claim 1, further comprising a plate-shaped first neutron absorber made of cadmium downstream of the heavy water layer.

3. The neutron control device according to claim 1, further comprising a lead plate disposed downstream of a first neutron absorber.

4. The neutron control device according to claim 1, further comprising a plate-shaped second neutron absorber containing boron or lithium provided around a first neutron absorber.

5. A neutron irradiation apparatus comprising:
 a proton beam introduction tube for introducing a proton beam;
 a target provided at a distal end of the proton beam introduction tube;
 a graphite body disposed around the target;
 the neutron control device according to claim 1; and
 a neutron moderation tank disposed to surround the graphite body and the neutron control device, into which tank a boric acid solution or another neutron moderator is introduced, wherein
 the neutron control device is disposed below the target.

* * * * *